United States Patent [19]

Yue et al.

[11] Patent Number: 5,504,017
[45] Date of Patent: Apr. 2, 1996

[54] VOID DETECTION IN METALLIZATION PATTERNS

[75] Inventors: John T. Yue, Los Altos; Shekhar Pramanick, Fremont, both of Calif.

[73] Assignee: Advanced Micro Devices, Inc., Sunnyvale, Calif.

[21] Appl. No.: 359,464

[22] Filed: Dec. 20, 1994

[51] Int. Cl.$^6$ .......................... H01L 71/66; G01N 25/72; G01N 27/20
[52] U.S. Cl. .............. 437/8; 437/957; 437/171; 374/5; 324/766
[58] Field of Search .................... 374/4, 5; 324/765, 324/766, 538; 437/170, 171, 8, 957

[56] References Cited

U.S. PATENT DOCUMENTS

| | | |
|---|---|---|
| 3,504,524 | 9/1966 | Maley . |
| 3,511,086 | 5/1970 | Woodmansee . |
| 3,803,413 | 4/1974 | Vanzetti et al. ............... 250/338 |
| 4,215,562 | 8/1980 | Gavrilin et al. . |
| 4,431,967 | 2/1984 | Nishioka . |
| 4,466,746 | 8/1984 | Hancock et al. . |
| 4,712,057 | 12/1987 | Pau .............................. 324/73 R |
| 5,229,311 | 7/1993 | Lai et al. . |
| 5,274,264 | 12/1993 | Yung ........................... 257/529 |
| 5,298,433 | 3/1994 | Furuyama . |
| 5,396,068 | 3/1995 | Bethea ........................ 250/330 |

FOREIGN PATENT DOCUMENTS

| | | | |
|---|---|---|---|
| 53-142170 | 12/1978 | Japan ............................ 437/170 |
| 824003 | 4/1981 | U.S.S.R. ....................... 374/4 |
| 857837 | 8/1981 | U.S.S.R. ....................... 374/4 |

OTHER PUBLICATIONS

Y.-S. Chaug et al., Japan J. Appl. Phys., 14, 3 (1975) 431 "Temperature Distribution in a Cracked Stripe".
H.-U. Schreiber et al., Solid State Electronics, 24, 12 (1981) 1135 "Electromizration Measuring techniques . . . ".
S. Wolf, "Silicon Processing for the VLSI Era" vol. II, 1992, pp. 121–133, 191, 264–267.
Levine et al., "Electromigration Induced Damage and Structure Change in Cr–Al/Cu and Al/Cu Interconnection Lines," 1984, IEEE, pp. 242–249.

Primary Examiner—Brian E. Hearn
Assistant Examiner—Leon Radomsky
Attorney, Agent, or Firm—Lowe, Price, LeBlanc & Becker

[57] ABSTRACT

Voids in a metallization pattern comprising a barrier layer, such as those generated by stress migration, are detected by applying a current across a test section of the metallization pattern to generate hot spots which are detected as by employing an infrared microscope or with a liquid crystalline material.

33 Claims, 1 Drawing Sheet

VOID DETECTION IN METALLIZATION PATTERNS

TECHNICAL FIELD

The present invention relates to the detection of voids in a metallization pattern containing a barrier layer. The invention has particular utility in detecting sub-surface voids generated by stress migration.

BACKGROUND ART

Conventional semiconductor devices having integrated circuitry normally comprise a plurality of openings characterized as "vias," "contacts," or "windows," in a dielectric layer. These openings are normally filled with a conductive material having low resistivity, such as a metal or polysilicon, to provide electrical connection through the dielectric material. For example, in many MOSFET fabrication techniques, after formation of the source, drain and gate, a dielectric is deposited over the transistor and an opening created above some or all the source and drain regions. A conductive material, such as aluminum, is deposited within the opening to effect electrical contact with the source or drain region. Thus, the conductive material in the opening provides a path for electrical contact between the source or drain region and a conductive material on the upper surface of the dielectric layer. Multilevel integrated circuits comprise a plurality of dielectric layers having openings filled with conductive material which provides electrical contact between conductive runners or lines beneath and above the additional dielectric layers.

In order to satisfy increasingly higher density requirements, the dimensions of integrated circuits are continuously reduced and, hence, the line widths of the conductors decreased into the submicron range. While the conductors become narrower and narrower, the stresses imposed upon the conductive material increase, thereby resulting in a high failure rate. Many of these failures stem from defects or voids generated by stress migration as a result of thermal stresses caused by exposure at different temperatures. Other types of voids are generated by electromigration and during various production steps, such as etching. These voids, which can range from 0.1 microns to about 10 microns or more, ultimately lead to failures in narrow electrical lines by causing open circuits.

The detection of voids in metallization patterns is a recognized objective in the art. However, this objective constitutes a perplexing problem which is not easily attained. A conventional technique employed to detect voids in metallization patterns involves the use of a scanning electron microscope. This technique is extremely time consuming and normally requires about a day to check one device. Another method which has been employed to detect voids in metallization patterns is an indirect method based upon resistance measurements. However, since a detected higher resistance can be attributed to multiple underlying causes, this method of void detection is not accurate.

A recently developed technique for detecting stress-induced voids is disclosed by Smith et al., "Direct Measurement of Stress-Induced Void Growth by Thermal Wave Modulated Optical Reflectance Imaging" IEEE/RPS 1990, pages 200–208. Smith et al. reveal a technique characterized as "thermal wave" modulated optical reflectance imaging which nondestructively detects voids within metallization patterns with submicron resolution. The thermal wave technique involves utilizing a laser beam and analyzing the reflected periodic waves of heat or thermal waves. The disadvantages of the "thermal wave" technique are multiple. A fundamental disadvantage of the "thermal wave" technique stems from the necessity of employing reflected laser light, which limits the minimum size of a metal line that can be imaged to the laser light wave length. Since a He-$N_2$ laser with a wave length of 628 nm is generally employed, the metal line width that can be imaged is restricted to about 0.6 microns. This constitutes a severe limitation on the "thermal wave" technique, since current technology involves metal lines less than 0.5 microns. Moreover, the "thermal wave" technique is highly cumbersome and cannot be practically employed in a manufacturing environment.

Apart from the previously mentioned scanning electron microscope and thermal wave technique, we are not aware of any method conventionally employed in the semiconductor industry to detect voids in metallization patterns. The disadvantages of such previously mentioned detection technique leaves the problem of detecting voids in metallization patterns acute, particularly in manufacturing high and ultra high density semiconductor devices.

A prior art non-destructive technique for detecting defects and electrical discontinuities comprises the application of a current to a test piece or section. A rise in temperature or "hot spot" occurs in the vicinity of the defect or discontinuity which can be visually detected.

Nishioka, U.S. Pat. No. 4,431,967, discloses a method for detecting minute defects on a semiconductor chip by applying a current to generate a hot spot and observing the hot spot using an optical microscope and a nematic liquid crystal film. Gavrilin et al., U.S. Pat. No. 4,215,562, disclose a method for detecting surface and sub-surface flaws in a rolled product by high frequency heating to produce a temperature gradient wherein a change of color is observed in a indicator coating. Woodmansee, U.S. Pat. No. 3,511,086, discloses a method for detecting voids and other discontinuities in a substrate by applying a cholesteric liquid crystalline material, thermal cycling and observing a color response. Burgess et al., "Improved Sensitivity for Hot Spot Detection Using Liquid Crystals," IEEE/IRPS 1984, pages 119–121, disclose a method for detecting defects employing a nematic liquid crystalline material. Maley, U.S. Pat. No. 3,504,525, discloses a nondestructive infrared technique for detecting voids and inclusions in material. Hancock et al., U.S. Pat. No. 4,466,746, disclose a detection technique employing a boiling liquid to detect hot spots in electronic circuitry, such as printed circuit boards and metallization patterns. The use of an infrared microscope is also disclosed. U.S. Pat. No. 5,298,433 discloses a screening method for testing an interconnection on a semiconductor wafer by judging whether or not the electrical characteristics of each chip area are acceptable through a die sort test and remedying an integrated circuit in a chip by means of the redundant circuit prior to assembly in an integrated circuit device.

A recent development in integrated circuitry comprises the use of a barrier layer or layers under and/or above the metallization layer for various reasons. One such device is disclosed by Lai et al. in U.S. Pat. No. 5,229,311. With reference to FIG. 1, the semiconductor device disclosed by Lai et al. comprises a substrate 13 provided with source region 11 and drain region 10, separated by field oxide isolation regions 15. Above channel region 12 is formed a first polysilicon layer which functions as a floating gate for the memory cell and a second polysilicon gate 17 which functions as a control gate separated by insulation 22, with 23 representing a thermally grown oxide layer over the source/drain and polygate surfaces. A planarizing dielectric film 18 is then deposited on the thermal oxide by a conventional chemical vapor deposition technique. A barrier metal layer 19 is then formed. Barrier metal layer 19 can comprise titanium or a titanium rich compound such as titanium nitride or titanium-tungsten. An aluminum metallization or bit line 20 is then formed and, subsequently, insulation layer 21 provided.

DISCLOSURE OF THE INVENTION

An object of the present invention is a method for detecting voids in a metallization pattern comprising a barrier layer.

A further object of the invention is the detection of voids in a metallization pattern comprising a material having a low resistivity and a barrier metal layer comprising a material having a high electrical resistivity.

Additional objects, advantages and other features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

According to the present invention, the foregoing and other objects are achieved in part by a method for detecting voids in a metallization pattern comprising a barrier layer by passing a current across the metallization pattern layer to generate hot spots in the vicinity of the voids and detecting the hot spots.

Another aspect of the present invention is a method for detecting voids in a metallization pattern comprising a material having a low electrical resistivity and a barrier layer comprising a material having a high electrical resistivity, wherein the voids are in the material having a low electrical resistivity, which method comprises passing a current across the metallization pattern to generate hot spots in the vicinity of the voids and detecting the hot spots.

Additional objects and advantages of the present invention will become readily apparent to those skilled in this art from the following detailed description, wherein only the preferred embodiment of the invention is shown and described, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE INVENTION

Figure 1:
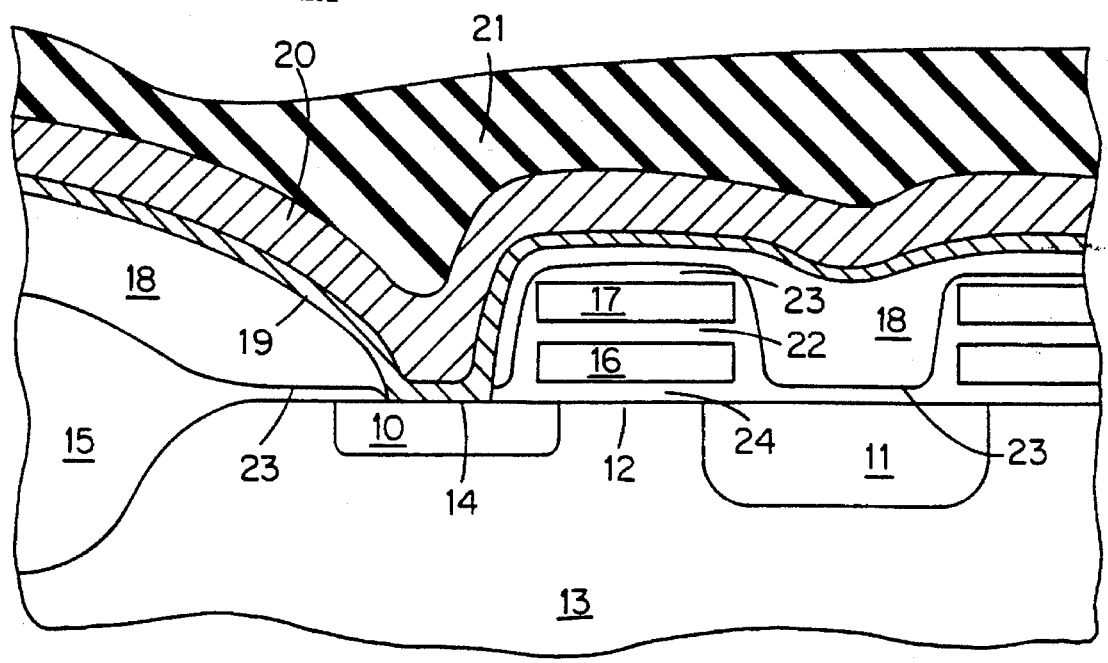
FIG. 1 is a cross-sectional view of a typical EEPROM device fabricated with a barrier layer.

The present invention is directed to a method of detecting voids in a metallization pattern of a semiconductor device, wherein the metallization pattern comprises a barrier layer. Most metallization patterns are made with a material having a relatively low electrical resistivity, such as aluminum which has an electrical resistivity of about $2.8 \times 10^{-6}$ ohm cm. If a current is applied across such a low electrical resistivity metallization pattern containing a void which forms a complete separation in the metallization pattern, such as a slit void, the applied current will not flow. If a current is applied across such a metallization pattern containing internal voids, the actual rise in temperature is insignificant due to the extremely low electrical resistivity of the metallization pattern.

We have discovered, however, that in a metallization pattern containing at least one barrier layer, it is possible to generate areas of detectable elevated temperature on the surface of the metallization pattern in the vicinity of voids by passing a current across the metallization pattern. After extensive investigation, we found that when a current is applied across such a metallization pattern containing voids and a barrier layer, the current is shunted to the barrier layer in the vicinity of the voids. Since the barrier layer materials normally exhibit a rather high electrical resistivity, the surface temperature of the metallization pattern in the vicinity of the voids is elevated to an appreciable extent which is readily detectable. Thus, we have found that voids in a metallization pattern comprising a barrier layer can be detected by passing a current across the metallization pattern to generate detectable hot spots. It is preferred to conduct the inventive method by passing a current across a metallization pattern comprising a barrier layer, thereby generating surface hot spots in the vicinity of the voids and detecting the hot spots employing a liquid crystalline material or an infrared microscope.

The present invention is applicable to any type of semiconductor device containing a metallization pattern comprising a barrier layer. The metallization patterns to which the present invention is applicable comprise conventional metallization configurations, such as metallization patterns comprising one or more barrier layers at the lowermost and/or uppermost part of the metallization patterns. The metallization pattern can also contain a barrier layer within the metallization pattern itself, such as in the central portion thereof. The barrier layer or layers preferably comprise a material having a relatively high electrical resistivity, most preferably an electrical resistivity of about $100 \times 10^{-6}$ to about $500 \times 10^{-6}$ ohm cm such as $20 \times 10^{-6}$ to about $500 \times 10^{-6}$ ohm cm, e.g., about $50 \times 10^{-6}$ to about $500 \times 10^{-6}$ ohm cm. The metallization pattern preferably comprises, in thickness, at least about 75% of a material having a relatively low electrical resistivity, most preferably about $0.5 \times 10^{-6}$ to about $15 \times 10^{-6}$ ohm cm, with about $0.5 \times 10^{-6}$ to about $10 \times 10^{-6}$ ohm cm particularly preferred and less than about 25% of the relatively high electrical resistivity material. In a preferred aspect of the present invention, the relatively low resistivity material comprises aluminum, copper, or an alloy thereof, most preferably aluminum or an aluminum alloy. In another preferred aspect of the present invention, the barrier layer comprises titanium, tungsten, tantalum their alloys and nitrides and mixtures thereof, preferably titanium and its alloys and nitrides.

The types of voids capable of detection by the present method include voids generated in a metallization pattern by inspection techniques, such as stress migration voids and electromigration voids. The present invention also enjoys utility in detecting voids generated during any of various processing techniques, such as metal deposition and etching. Voids capable of detection by the present invention include surface voids, slit voids and internal voids. Voids capable of detection by the present invention include those ranging in size from about 0.1 micron to about 10 microns.

In conducting the present invention, it is possible to generate regions of elevated temperature on the surface of metallization patterns in the vicinity of voids, above the temperature of the surface of the metallization patterns which do not contain voids. The resulting temperature difference depends upon the current density or applied current. The present invention can be conducted using a current density of from about $0.1 \times 10^6$ to about $200 \times 10^6$ amperes/cm$^2$. Normally, a current density of about $0.5 \times 10^6$ to about $100 \times 10^6$ amperes/cm$^2$ is employed, preferably a current density of about $0.75 \times 10^6$ to about $30 \times 10^6$ amperes/cm$^2$, most preferably a current density of about $1 \times 10^6$ to about $20 \times 10^6$ amperes/cm$^2$.

Figure 2:
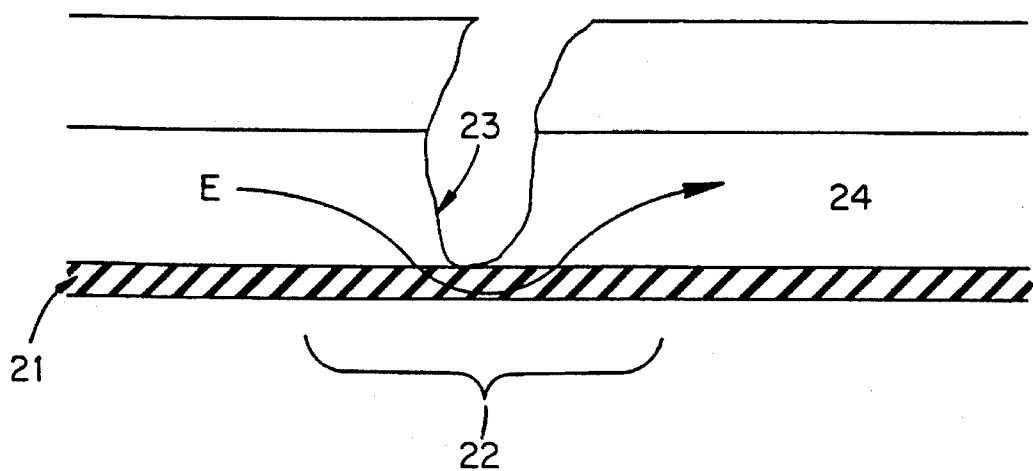
FIG. 2 schematically shows the generation of a hot spot in accordance with the present invention.

Upon application of a current to a metallization pattern containing a void, such as a slit void generated by stress migration, the current path is shunted to the barrier layer, thereby generating an elevated temperature at the surface of the metallization pattern in the vicinity of such void due to the higher electrical resistivity of the barrier layer. As shown in FIG. 2, current E is shunted to barrier layer 21 to generate a hot spot 22 in the vicinity of slit void 23 in dielectric layer 24. The resulting hot spot can be detected by coating the surface of the metallization pattern with a conventional liquid crystalline material and observing a calorimetric response. Suitable liquid crystalline materials include nematic and cholesteric materials. It is preferred to employ a nematic liquid crystalline material known as K18, i.e., 4 cyano 4' hexyl-biphenyl, because of its desirable combination of properties. The voltage applied can be pulsed to obtain the known blinking effect as disclosed by Burgess et al. previously mentioned. The hot spot can also be detected by employing an infrared microscope, preferably by mounting the microscope in a conventional manner to effect scanning.

Thus, the present invention can be employed to screen potential test failures in semiconductor devices by detecting voids in metallization patterns containing a barrier layer. Semiconductor devices, including those in the wafer stage, can be easily screened, thereby minimizing costs. The present invention has application to any type of semiconductor device comprising a metallization pattern having a barrier layer.

Only the preferred embodiment of the invention and but a few examples of its versatility are shown and described in the present disclosure. It is to be understood that the invention is capable of use in various other combinations and environments and is capable of changes or modifications within the scope of the inventive concept as expressed herein.

We claim:

1. A method of detecting voids in a metallization pattern of a semiconductor device, which metallization pattern contains an interconnection line and a barrier layer and voids are detected in the interconnection line by measuring hot spots in the barrier layer, comprising:

applying a current across a test section of the metallization pattern, whereby hot spots in the barrier layer cause an elevation in temperature in regions on the surface of the metallization pattern in the vicinity of the voids; and detecting the areas of elevated temperature.

2. The method according to claim 1, wherein the barrier layer comprises a material selected from the group consisting of titanium, tungsten, tantalum, alloys thereof, nitrides thereof and mixtures thereof.

3. The method according to claim 1, wherein the regions of elevated temperature are detected with an infrared microscope.

4. The method according to claim 3, wherein the regions of elevated temperature are detected by scanning the test section with an infrared microscope.

5. The method according to claim 4, wherein the infrared microscope is mounted to enable automated detection of areas of elevated temperature.

6. The method according to claim 1, wherein the regions of elevated temperature are detected by applying a liquid crystalline material to the surface of the test section and observing a colorimetric change in the liquid crystalline material.

7. The method according to claim 6, wherein the liquid crystalline material is a nematic liquid crystalline material.

8. The method according to claim 6, wherein the liquid crystalline material is a cholesteric crystalline material.

9. The method according to claim 1, wherein the voids are generated by stress migration.

10. The method according to claim 1, wherein the voids are generated by electromigration.

11. The method according to claim 1, wherein the voids are generated by a processing technique.

12. The method according to claim 11, wherein the voids are generated by etching.

13. The method according to claim 1, wherein the voids are about 0.1 micron to about 10 microns or greater.

14. The method according to claim 1, wherein the interconnection line comprises a material having a relatively low electrical resistivity and the barrier layer comprises a material having a relatively high electrical resistivity, and wherein the voids are located in the low electrical resistivity material.

15. The method according to claim 14, wherein the low electrical resistivity material comprises a metal selected from the group consisting of aluminum, copper, and alloys thereof, and the high electrical resistivity material comprises a material selected from the group consisting of titanium, tungsten, alloys thereof, nitrides thereof and mixtures thereof.

16. The method according to claim 15, wherein the low electrical resistivity material comprises aluminum or an alloy thereof, and the high electrical resistivity material comprises titanium, an alloy thereof or a nitride thereof.

17. The method according to claim 14, wherein the low electrical resistivity metal has an electrical resistivity of about $0.5 \times 10^{-6}$ to about $10 \times 10^{-6}$ ohm cm, and the high electrical resistivity material has an electrical resistivity of about $50 \times 10^{-6}$ to about $500 \times 10^{-6}$ ohm cm.

18. The method according to claim 14, wherein the low electrical resistivity material comprises at least about 75% of the thickness of the metallization pattern.

19. The method according to claim 1, wherein the barrier layer comprises a plurality of layers.

20. The method according to claim 1, wherein the barrier layer is formed at the bottommost part of the metallization pattern.

21. The method according to claim 20, wherein a barrier layer is also formed at the uppermost part of the metallization pattern.

22. The method according to claim 20, wherein a barrier layer is also formed within the metallization pattern.

23. The method according to claim 1, wherein the current density is about $0.1 \times 10^6$ to about $2 \times 10^6$ amperes/cm$^2$.

24. The method according to claim 23, wherein the current density is about $0.5 \times 10^6$ to about $100 \times 10^6$ amperes/cm$^2$.

25. The method according to claim 24, wherein the current density is about $0.75 \times 10^6$ to about $30 \times 10^6$ amperes/cm$^2$.

26. The method according to claim 25, wherein the current density is about $1\times10^6$ to about $20\times10^6$ amperes/cm$^2$.

27. The method according to claim 1, wherein the voids are in the surface of the metallization pattern.

28. The method according to claim 1, wherein the voids are internal voids.

29. The method according to claim 22, wherein the barrier layer is formed in the central part of the metallization pattern.

30. The method according to claim 16, wherein the high electrical resistivity material comprises titanium nitride.

31. The method according to claim 14, wherein the low electrical resistivity metal has an electrical resistivity of about $0.5\times10^{-6}$ to about $15\times10^{-6}$ ohm cm, and the high electrical resistivity material has an electrical resistivity of about $20\times10^{-6}$ to about $500\times10^{-6}$ ohm cm.

32. The method according to claim 14, wherein the low electrical resistivity metal has an electrical resistivity of about $0.5\times10^{-6}$ to about $10\times10^{-6}$ ohm cm.

33. The method according to claim 32, wherein the high electrical resistivity material has an electrical resistivity of about $50\times10^{-6}$ to about $500\times10^{-6}$ ohm cm.

* * * * *